US006410254B1

(12) United States Patent
Finer et al.

(10) Patent No.: US 6,410,254 B1
(45) Date of Patent: Jun. 25, 2002

(54) COMPOSITIONS AND ASSAYS UTILIZING ADP OR PHOSPHATE FOR DETECTING PROTEIN MODULATORS

(75) Inventors: Jeffrey T. Finer, Foster City; Fady Malik, Burlingame; Roman Sakowicz, Foster City; Christopher Shumate, San Francisco; Kenneth Wood, Foster City, all of CA (US)

(73) Assignee: Cytokinetics, South San Francisco, CA (US)

( * ) Notice: Subject to any disclaimer, the term of this patent is extended or adjusted under 35 U.S.C. 154(b) by 0 days.

(21) Appl. No.: 09/314,464

(22) Filed: May 18, 1999

(51) Int. Cl.[7] ............................. C12Q 1/42; C12Q 1/48; C12Q 1/52; C12Q 1/50; C12N 9/18

(52) U.S. Cl. ............................. 435/21; 435/15; 435/16; 435/17; 435/18; 435/19; 435/23; 435/24; 435/196

(58) Field of Search .............................. 435/21, 15, 17, 435/18, 19, 23, 24, 196

(56) References Cited

U.S. PATENT DOCUMENTS

| | | | |
|---|---|---|---|
| 4,923,796 A | 5/1990 | Deneke et al. | 435/15 |
| 5,283,173 A | 2/1994 | Fields et al. | 435/252.3 |
| 5,468,614 A | 11/1995 | Fields et al. | 435/6 |
| 5,525,490 A | 6/1996 | Erickson et al. | 435/29 |
| 5,667,973 A | 9/1997 | Fields et al. | 435/6 |
| 5,673,463 A | 10/1997 | Chih-wen | 24/265 |
| 5,759,795 A | 6/1998 | Jubin | 435/21 |
| 6,207,403 B1 | 3/2001 | Goldstein et al. | 435/21 |

OTHER PUBLICATIONS

Field et al., "A novel genetic system to detect protein–protein interactions," *Nature*, 340:245–246 (1989).
Vasavada et al., "A contingent replication assay for the detection of protein–protein interactions in animal cells," *PNAS USA*, 88:10686–10690 (1991).
Fearon et al., "Karyoplasmic interaction selection strategy: A general strategy to detect protein–protein interactions in mammalian cells," *PNAS USA*, 89:7958–7962 (1992).
Dang et al., "Intracellular Leucine Zipper Interactions Suggest c–Myc Hetero–Oligomerization" *Mol. Cell. Biol.*, 11:954–962 (1991).
Chien et al., "The two–hybrid system: A method to identify and clone genes for proteins that interact with a protein of interest," *PNAS USA*, 88:9578–9582 (1991).
Webb, "A continuous spectrophotometric assay for inorganic phosphate and for measuring phosphate release kinetics in biological systems," *PNAS USA*, 89:4884–4887 (1992).
Ungerer et al., "An enzymatic assay of inorganic phosphate in serum using nucleoside phosphorylase and xanthine oxidase," *Elsevier Clinica Chimica Act.*, 223:149–157 (1993).
Rieger et al., "A Continuous Spectrophotometric Assay for Asparte Transcarbamylase and ATPases," *Anal. Biochem.*, 246:86–95 (1997).
Brune et al., "Direct, Real–Time Measurement of Rapid Inorganic Phosphate Release Using a Novel Fluorescent Probe and Its Application to Actomyosin Subfragment 1 ATPase," *Biochem.*, 33:8262–8271 (1994).
Hackney, "The Rate–limiting Step in Microtubule–stimulated ATP Hydrolysis by Dimeric Kinesin Head Domains Occurs while Bound to the Microtubule," *J. Biol. Chem.*, 269(23):16508–16511 (1994).
Greengard, "Determination of Intermediary Metabolites by Enzymic Fluorimetry," *Nature*, 178:632–634 (1956).
Banik et al., "A continuous fluorimetric assay for ATPase activity," *Biochem. J.*, 266:611–614 (1990).
Fiske et al., "The Colorimetric Determination of Phosphates," *J. Biol. Chem.*, 66:375–400 (1925).
Goldstein, "With Apologies to Scheherazade: Tails of 1001 Kinesin Motors," *Annu. Rev. Genet.*, 27:319–351 (1993).
Desai et al., "Kin I Kinesins Are Microtubule–Destablizing Enzymes," *Cell*, 96:69–78 (1999).
Walczak et al., "XKCM1: A Xenopus Kinesin–Related Protein That Regulates Microtubule Dynamics during Mitotic Spindle Assembly," *Cell*, 84:37–47 (1996).
Ronaghi et al., "Real–Time DNA Sequencing Using Detection of Pyrophosphate Release," *Analytical Biochemistry*, 242:84–89 (1996).
Ronaghi et al, "A Sequencing Method Based on Real–Time Pyrophosphate," *Science*, 281:363–365 (1998).
Wood et al., "Plus End–Directed Microtubule Motor Required for Chromosome Congression," PCT application claiming priority to U.S.S.N. 06/058,645 filed Sep. 11, 1997.

*Primary Examiner*—Tekchand Saidha
(74) *Attorney, Agent, or Firm*—Beyer Weaver & Thomas, LLP; Lauren L. Stevens, Esq.

(57) ABSTRACT

Described herein are methods which identify candidate agents as binding to a protein or as a modulator of the binding characteristics or biological activity of a protein. Generally, the methods involve the use of ADP or phosphate. The assays can be used in a high throughput system to obviate the cumbersome steps of using gels or radioactive materials.

38 Claims, No Drawings

COMPOSITIONS AND ASSAYS UTILIZING ADP OR PHOSPHATE FOR DETECTING PROTEIN MODULATORS

FIELD OF INVENTION

This invention is related to the use of adenosine diphosphate (ADP) or phosphate in assays for identifying compounds which bind to or modulate the binding characteristics or biological activity of a protein.

BACKGROUND OF THE INVENTION

Drugs and other compounds intended for use in the diagnosis, cure, mitigation, treatment or prevention of disease in man or other animal or for use in the agricultural arena, have made a significant impact on the practice of modem medicine and on the agricultural arena. In some cases, such as in the development of vaccines, drugs have essentially eradicated once untreatable diseases. In the case of the agriculture, compounds have been developed which both extend the life and/or volume of produce as well as kill unwanted plants where desirable. Therefore, the development of these compounds is of great interest.

Many useful compounds modulate the physical interaction of proteins. Traditionally, these protein-protein interactions have been evaluated using biochemical techniques, including chemical cross-linking, co-immunoprecipitation, co-fractionation and co-purification. Recently genetic systems have been invented to detect protein-protein interactions. The first work was done in yeast systems, and was termed the "yeast two-hybrid" system. The basic system requires a protein-protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463.

In another approach to drug discovery, studies are designed to determine the biological activity of a protein. For example, the conditions such as the specific substrate or stimulator required for an enzymatic reaction are investigated. Moreover, there are a number of studies designed specifically for aide in the detection step in these assays. For example, one study discloses a spectrophotometric assay for inorganic phosphate (Pi) to probe the kinetics of Pi release from biological systems such as GTPases and ATPases. Webb, PNAS, 89:4884–4887 (1992). Another study reports on an enzymatic assay of inorganic phosphate in serum using nucleoside phosphorylase and xanthine oxidase. Ungerer, et al., Elsevier Clinica Chimica Act, 223:149–157 (1993). A continuous spectrophotometric assay for aspartate transcarbamylase and ATPases is reported on in Rieger, et al., Anal. Biochem., 246:86–95 (1997). There is also a study which reports on the measurement of inorganic phosphate release using fluorescent probes and its application to actomysin subfragment 1 ATPase. Brune, et al., Biochem., 33:8262–8271 (1994). U.S. Pat. No. 4,923,796 discloses a method for quantitative enzymatic determination of ADP. Microtubule-stimulated adenosine triphosphate (ATP) hydrolysis by kinesin is discussed in Hackney, J. Biol. Chem., 269(23):16508–16511 (1994). Furthermore, enzymatic fluorimetry and fluorimetric assays for ATPase activity are reported on in Greengard, Nature, 178:632–634 (1956) and Utpal and Siddhrtha, Biochem. J., 266:611–614 (1990), respectively.

In a different approach, modulators of an enzymatic reaction are investigated, wherein the conditions which allow the enzymatic reaction to occur are already known. For example, U.S. Pat. No. 5,759,795 discloses an assay for identifying an inhibitor of a Hepatitis C Virus NS3 protein ATPase which involves a luciferase reaction. Luciferase reactions are known in the art. In the case of an ATPase inhibitor, the presence of an ATPase inhibitor is indicated when ATP is available to drive the oxidation of luciferon by luciferase. This approach requires ATP but does not re-generate ATP.

Thus, while efforts have been made toward drug discovery, more efficient means are desirable. In particular, there is a need for an efficient system which can distinguish between a compound directly binding to a second component, or whether the compound modulates the binding between two other components, or whether the compound modulates the biological activity of a known enzymatic reaction. Accordingly, it is an object of the present invention to provide methods of identifying compounds which either bind to or which modulate the binding characteristics or the biological activity of a target protein. It is also an object to provide compositions for use in the assays provided herein.

SUMMARY OF THE INVENTION

The present invention provides methods which identify candidate agents that bind to a protein or act as a modulator of the binding characteristics or biological activity of a protein. In one embodiment, the method is performed in plurality simultaneously. For example, the method can be performed at the same time on multiple assay mixtures in a multi-well screening plate as further described below. Furthermore, in a preferred embodiment, fluorescence or absorbance readouts are utilized to determine enzymatic activity. Thus, in one aspect, the invention provides a high throughput screening system.

In one embodiment, the present invention provides a method of identifying a candidate agent as a modulator of the activity of a target protein. The method comprises adding a candidate agent to a mixture comprising a target protein which directly or indirectly produces ADP or phosphate under conditions which normally allow the production of ADP or phosphate. The method further comprises subjecting the mixture to an enzymatic reaction which uses said ADP or phosphate as a substrate under conditions which normally allow the ADP or phosphate to be utilized and determining the level of activity of the enzymatic reaction. A change in the level between the presence and absence of the candidate agent indicates a modulator of the target protein.

In one aspect, the target protein indirectly produces the ADP or phosphate by producing a substrate for a reaction which produces the ADP or phosphate. In another aspect, the target protein indirectly produces phosphate or ADP or phosphate by regulating an enzyme which produces ADP or phosphate. In yet a further aspect, the target protein directly produces phosphate or ADP.

In another aspect, the invention provides a method of identifying a candidate agent as a modulator of the activity of a target protein wherein the target protein uses ADP or phosphate directly or indirectly. The method comprises adding a candidate agent to a mixture comprising the target protein under conditions which normally allow the utilization of ADP or phosphate. The method further comprises determining the level of utilization wherein a change in the level between the presence and absence of the candidate agent indicates a modulator of the target protein.

In another embodiment provided herein is a method for identifying whether any two target proteins interact. The method comprises providing a first target chimera comprising a functional molecular motor binding domain and a first target protein. The method further comprises providing a second target chimera comprising a functional microtubule stimulated ATPase domain and a second target protein. Additionally, the method comprises combining the first and second target chimeras under conditions which normally allow activity of a motor protein which comprises a molecular motor binding domain and a microtubule stimulated ATPase domain, wherein an increase in motor protein activity indicates interaction between the two target proteins.

In a further embodiment a method is provided for identifying whether a candidate agent is a modulator of at least one of any two target proteins. The method comprises providing a first target chimera comprising a functional molecular motor binding domain and a first target protein and further providing a second target chimera comprising a functional microtubule stimulated ATPase domain and a second target protein. Additionally, the method comprises combining the first and second target chimeras in the presence and absence of a candidate, wherein a change in motor protein activity, which requires both a molecular motor binding domain and a microtubule stimulated ATPase, between the presence and absence of a candidate agent indicates the candidate agent is a modulator of at least one of the target proteins.

Additionally, provided herein is a chimeric protein comprising a functional molecular motor binding domain and a target binding domain wherein the chimeric protein is independent of a functional microtubule stimulated ATPase domain. Also provided herein is a chimeric protein comprising a functional microtubule stimulated ATPase domain and a target binding domain, wherein the chimeric protein is independent of a functional molecular motor binding domain.

In one aspect, a nucleic acid comprising a nucleic acid encoding a chimeric protein in accordance with the present invention is provided. In another aspect a cell comprising a nucleic acid or a chimeric protein in accordance with the present invention is provided.

DESCRIPTION OF THE PREFERRED EMBODIMENTS

The present invention provides methods for the identification of candidate agents that bind to a target protein or serve as modulators of the biological activity of a target protein. These assays utilize various methods to measure, in ways amenable to high throughput screening, the generation or consumption of ADP or phosphate. That is, target proteins that either directly or indirectly produce or consume ADP or phosphate may be screened in the present invention. Thus, by providing assay systems that rapidly, efficiently and inexpensively assay ADP or phosphate, modulators (including both antagonists and agonists) of any test protein that directly or indirectly produces ADP or phosphate may be found. The present invention thus utilizes high throughput assays that obviate the traditional cumbersome steps of using gels or radioactive materials.

Accordingly, the present invention provides methods of screening of target proteins. By "target protein" herein is meant a protein that directly or indirectly produces ADP or phosphate. The target proteins can be from eukaryotes or procaryotes, including mammals, fungi, bacteria, insects, and plants, as well as viruses. In a preferred embodiment, the target proteins are from mammalian cells, with rodents (mice, rats, hamsters, guinea pigs and gerbils being preferred), primates and humans being preferred, and humans being particularly preferred.

"Protein" in this context means a compound that comprises at least two covalently attached amino acids and includes proteins, polypeptides, oligopeptides and peptides. The proteins may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

Suitable target proteins, include, but are not limited to, cytoskeletal proteins including, but not limited to, kinesins, myosins, tubulins, actins, tropomyosins, and troponins, with human proteins being preferred.

In a preferred embodiment, the target protein is a kinesin, including mitotic kinesins. Mitotic kinesins are enzymes essential for assembly and function of the mitotic spindle, but are not generally part of other microtubule structures, such as nerve processes. Mitotic kinesins play essential roles during all phases of mitosis. These enzymes are "molecular motors" that translate energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest. From both the biological and enzymatic perspectives, these enzymes are attractive targets for the discovery and development of novel anti-mitotic chemotherapeutics.

Suitable kinesins include, but are not limited to, Kin2, chromokinesin, Kif1A, KSP, CENP-E, MCAK, HSET and Kif15 is provided. K335, Q475, D679, FL1, P166, H195, FL2, E433, R494, E658, L360, K491, S553, M329, T340, S405, V465, T488, M1, M2, M3, M4, M5, M6, FL3, A2N370, A2M511, K519, E152.2, Q151.2, Q353, M472 and MKLP1. It is understood that unless a particular species is named, the term "kinesin" includes homologs thereof which may have different nomenclature among species. For example, the human homolog of Kif1A is termed ATSV, the human homologue of Xenopus Eg5 is termed KSP, and human HSET corresponds to Chinese hamster CHO2.

By "kinesin protein activity" or grammatical equivalents herein is meant one of kinesin protein's biological activities, including, but not limited to, its ability to affect ATP hydrolyzation. Other activities include microtubule binding, gliding, polymerazation/depolymerazation (effects on microtubule dynamics), binding to other proteins of the spindle, binding to proteins involved in cell-cycle control, or serving as a substrate to other enzymes, such as kinases or proteases and specific kinesin cellular activities such as chromosome congregation, axonal transport, etc.

Methods of performing motility assays are well known to those of skill in the art (see, e.g., Hall, et al. (1996), *Biophys. J.*, 71: 3467–3476, Turner et al., 1996, *Anal. Biochem.* 242 (1):20–5; Gittes et al., 1996, *Biophys. J.* 70(1): 418–29; Shirakawa et al., 1995, *J. Exp. Biol.* 198: 1809–15; Winkelmann et al., 1995, *Biophys. J.* 68: 2444–53; Winkelmann et al., 1995, *Biophys. J.* 68: 72S, and the like).

In a preferred embodiment, the target protein directly or indirectly produces ADP and/or phosphate. Included in the definition of adenosine diphosphate (ADP) are ADP analogs, including, but not limited to, deoxyadenosine diphosphate (dADP) and adenosine analogs. As used herein, phosphate is used interchangeably with inorganic phosphate.

In a preferred embodiment, the target protein directly produces ADP or phosphate. In a preferred embodiment, the target protein is an enzyme having activity which produces ADP and/or phosphate as a reaction product. For example, proteins which directly produce ADP include but are not limited to ATPases, kinases, GTPases, phosphatases and phosphorylases. Suitable ATPases include, but are not limited to, myosins, kinesins, dyneins, DNA gyrase, DNA helicase, topoisomerase I and II, Na+-K+ ATPase, Ca2+ ATPase, F1 subunit of ATP synthase, terminase/DNA packaging protein; recA, heat shock proteins, NSF, katanin, SecA, 5-lipoxygenase, and actin. Suitable kinases include, but are not limited to, tyrosine kinases; serine-threonine kinases; receptor tyrosine kinases; growth factor receptors including but not limited to insulin receptor, epidermal growth factor receptor, platelet derived growth factor receptor and fibroblast growth factor receptor; ErbB2; calmodulin dependent protein kinases; protein kinase A; protein kinase C; myosin light chain kinase; CDK2 kinase; ROCK1 kinases; Src kinases; phosphorylase kinase; CheA; adenylate kinase; glycolytic kinases; EIF-2 alpha protein kinases; and Abl. Suitable GTPases include, but are not limited to, G proteins, Rho family GTPases: cdc42, RalA, RhoA and Rac1; Ras proteins; elongation factors including EF1α, EF1βγ, EF-Tu and EF-G; septins; tubulin; ARF related GTPase; rab; SSRP receptor; rhodopsin; transducin; and GTPase activating protein (GAP). Suitable phosphatases include, but are not limited to, protein phosphatases; myosin phosphatase; IP3 phosphatase; pyrophosphatase; and Cdc25. Suitable phosphorylases include, but are not limited to, polynucleotide phosphorylase and glycogen phosphorylase.

By "ATPase" herein is meant an enzyme that hydrolyzes ATP. For example, ATPases include proteins comprising molecular motors such as kinesins, myosins and dyneins. "Molecular motor" is a molecule that utilizes chemical energy to produce mechanical force or movement; molecular motors are particularly of interest in cytoskeletal systems. For further review, see, Vale and Kreis, 1993, GUIDEBOOK TO THE CYTOSKELETAL AND MOTOR PROTEINS New York: Oxford University Press; Goldstein, 1993, Ann. Rev. Genetics 27: 319–351; Mooseker and Cheney, 1995, Annu. Rev. Cell Biol. 11: 633–675; Burridge et al., 1996, Ann. Rev. Cell Dev. Biol. 12: 463–519.

In one embodiment, the target protein indirectly produces ADP or phosphate. In one aspect, a target protein indirectly produces ADP or phosphate by producing a product that then serves as a substrate in a subsequent enzymatic reaction for producing ADP or phosphate. For example, in a preferred embodiment, the target protein can be a pyrophosphate producing enzyme. Suitable pyrophosphate producing enzymes include, but are not limited to, DNA polymerases; RNA polymerases; reverse transcriptase; DNA ligase; adenylate cyclase; guanylate cyclase; PRPP synthetase; TRNA synthetases; acyl CoA synthetase and acetyl CoA carboxylase. Similarly, some ATPases produce AMP that can then be used to make ADP.

In another embodiment, the target protein is a synthase. Thus, preferred substrates for producing phosphate include pyrophosphate and any of the mono-, di- and triphosphate versions of CTP, UTP, GTP, ATP, and TTP, as well as derivatives including dideoxy derivatives. Additionally, other sources of substrates that can be cleaved to phosphate include phosphorylated peptides, oligonucleotides, carbohydrates, lipids, etc. For example, inositol triphosphate (IP3) is an important signaling moiety. Accordingly, any target protein which produces these compounds or others that can be used to produce phosphate or ADP may be assayed using the methods of the present invention.

In another aspect, a target protein indirectly produces ADP or phosphate by regulating an enzyme which produces phosphate or ADP. For example, the target can be an activator of an ATPase, such as an actin filament or a microtubule; thus in this embodiment, the target protein may be a protein polymer or oligomer. Alternatively, the target protein can be a filament binding protein or regulatory protein. For example, the regulatory protein can be the troponin-tropomyosin complex which regulates the binding of myosin to actin. Since myosin's ATPase is activated by binding to actin, modulators of this regulatory protein complex can be identified by the methods provided herein.

In a preferred embodiment, the target protein may consume ADP or phosphate; that is, rather than looking for an increase in signal, a loss of signal may be monitored.

Also included within the definition of the target proteins of the present invention are amino acid sequence variants of wild-type target proteins. These variants fall into one or more of three classes: substitutional, insertional or deletional variants. As for the target proteins as discussed below, these variants ordinarily are prepared by site specific mutagenesis of nucleotides in the DNA encoding the target protein, using cassette or PCR mutagenesis or other techniques well known in the art, to produce DNA encoding the variant, and thereafter expressing the DNA in recombinant cell culture as outlined above. However, variant target protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the target protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed variants screened for the optimal combination of desired activity. Techniques for making substitution mutations at predetermined sites in DNA having a known sequence are well known, for example, M13 primer mutagenesis and PCR mutagenesis. Screening of the mutants is done using assays of target protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the target protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Jyr |
| Ser | Thr |
| Thr | Ser |
| Tm | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity, although variants also are selected to modify the characteristics of the target proteins as needed. Alternatively, the variant may be designed such that the biological activity of the target protein is altered. For example, glycosylation sites may be altered or removed.

Further included within the definition of the target proteins of the invention are covalent modifications of the target proteins. One type of covalent modification includes reacting targeted amino acid residues of a target protein with an organic derivatizing agent that is capable of reacting with selected side chains or the N- or C-terminal residues of a target protein. Derivatization with bifunctional agents is useful, for instance, for crosslinking the target protein to a water-insoluble support matrix or surface. Commonly used crosslinking agents include, e.g., 1,1-bis(diazoacetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T.E. Creighton, Proteins: Structure and Molecular Properties, W.H. Freeman & Co., San Francisco, pp. 79–86 (1983)], acetylation of the N-terminal amine, and amidation of any C-terminal carboxyl group.

Another type of covalent modification of the target proteins included within the scope of this invention comprises altering the native glycosylation pattern of the polypeptide. "Altering the native glycosylation pattern" is intended for purposes herein to mean deleting one or more carbohydrate moieties found in the target native sequence, and/or adding one or more glycosylation sites that are not present in the native sequence.

Addition of glycosylation sites to target polypeptides may be accomplished by altering the amino acid sequence thereof. The alteration may be made, for example, by the addition of, or substitution by, one or more serine or threonine residues to the native sequence (for O-linked glycosylation sites). The target amino acid sequence may optionally be altered through changes at the DNA level, particularly by mutating the DNA encoding the target polypeptide at preselected bases such that codons are generated that will translate into the desired amino acids.

Another means of increasing the number of carbohydrate moieties on the target polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259–306 (1981).

Removal of carbohydrate moieties present on the targget polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Another type of covalent modification of target proteins comprises linking the target polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Target polypeptides of the present invention may also be modified in a way to form chimeric molecules comprising a target protein fused to another, heterologous polypeptide or amino acid sequence, a preferred embodiment of which is is described more fully below. In one embodiment, such a chimeric molecule comprises a fusion of a target polypeptide with a tag polypeptide which provides an epitope to which an anti-tag antibody can selectively bind. The epitope tag is generally placed at the amino-or carboxyl-terminus of the target polypeptide. The presence of such epitope-tagged forms of a target polypeptide can be detected using an antibody against the tag polypeptide. Also, provision of the epitope tag enables the target polypeptide to be readily purified by affinity purification using an anti-tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology, 6:1204–1210 (1988)]; the KT3 epitope peptide [Martin et al., Science, 255:192–194 (1992)]; tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)].

As will be appreciated by those in the art, the target proteins can be made in a variety of ways, including both synthesis de novo and by expressing a nucleic acid encoding the target protein.

Numerous suitable methods for recombinant protein expression, including generation of expression vectors, generation of fusion proteins, introducing expression vectors into host cells, protein expression in host cells, and purification methods are known to those in the art and are described, for example, in the following textbooks: Sambrook et al., *Molecular Cloning: A Laboratory Manual* (New York: Cold Spring Harbor Laboratory Press, 1989), Ausubel et al., *Short Protocols in Molecular Biology* (John Wiley & Sons, Inc., 1995), Harlow and Lane, *Antibodies: A Laboratory Manual* (New York: Cold Spring Harbor Laboratory Press, 1988), O'Reilly et al., *Baculovirus Expression Vectors: A Laboratory Manual* (New York: Oxford University Press, 1994), Richardson, *Baculovirus Expression Protocols* (Totowa: Humana Press, 1995), Kriegler, *Gene Transfer and Expression: A Laboratory Manual* (New York: Oxford University Press, 1991), Roth, *Protein Expression in Animal Cells, Methods in Cell Biology* Vol. 43 (San Diego: Academic Press, 1994), Murray, *Gene Transfer and Expression Protocols, Methods in Molecular Biology*, Vol 7 (Clifton: Humana Press, 1991), Deutscher, *Guide to Protein Purification, Methods in Enzymology* Vol. 182 (San Diego: Academic Press, Inc., 1990), Harris and Angal, *Protein Purification Methods: A Practical Approach* (Oxford: IRL Press at Oxford University Press, 1994), Harris and Angal, *Protein Purification Applications: A Practical Approach* (Oxford: IRL Press at Oxford University Press, 1990), Rees et al., *Protein Engineering. A Practical Approach* (Oxford: IRL Press at Oxford University Press, 1992) and White, *PCR Protocols, Methods in Molecular Biology*, Vol. 15 (Totowa, Humana Press, 1993).

The selection of host cell types for the expression of target proteins will depend on the target protein, with both eukaryotic and procaryotic cells finding use in the invention. Appropriate host cells include yeast, bacteria, archebacteria, fungi, plant, insect and animal cells, including mammalian cells. Of particular interest are *Drosophila melangaster* cells, *Saccharomyces cerevisiae* and other yeasts, *E. coli, Bacillus subtilis*, SF9 cells (and other related cells for use with baculoviral expression systems), C129 cells, 293 cells, Neurospora, BHK, CHO, COS, Dictyostelium, etc.

In a preferred embodiment, the target proteins are purified for use in the assays, as outlined herein, to provide substantially pure samples. By "substantially pure" or "isolated" herein is meant that the protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. Alternatively, the target protein need not be substantially pure as long as the sample comprising the target protein is substantially free of other components that can contribute to the production of ADP or phosphate (or, in the case of indirect assays, other components which are subsequently assayed).

The target proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the target protein may be purified using a standard anti-target antibody column. Ultrafiltration and diafiltration techniques, in conjunction with protein concentration, are also useful. For general guidance in suitable purification techniques, see Scopes, R., Protein Purification, Springer-Verlag, N.Y. (1982).

Suitable purification schemes for some specific kinesins are outlined in U.S. Ser. No. 09/295,612, filed Apr. 20, 1999, hereby expressly incorporated herein in its entirety, along with referenced materials.

The present invention provides methods for screening for modulators of target proteins. By "modulators" herein is meant both antagonists and agonists of the target protein. Thus, "modulating the activity of the target protein" includes an increase in target protein activity, a decrease in target protein activity, or a change in the type or kind of activity present. Generally, the modulator will both bind to the target protein (although this may not be necessary), and alter its biological or biochemical activity as defined herein. For inhibitors, changes of 25%, 50%, 75% and most preferably 100% of at least one biological activity of the target protein is seen. For activators, preferably the change is a change of at least 40%, more preferably at least 60%, more preferably at least 80%, more preferably at least 100%, more preferably at least 200%, and most preferably by at least 500%.

Accordingly, the present invention provides methods for screening candidate bioactive agents for the ability to modulate a target protein's activity. By "candidate agent" or "candidate bioactive agent" or "drug candidate" or grammatical equivalents herein is meant any molecule, e.g., protein, oligopeptide, small organic molecule, polysaccharide, polynucleotide to be tested in a screening assay.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines (including derivatives, structural analogs, or combinations thereof), derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In an embodiment provided herein, the candidate bioactive agents are proteins. The protein may be made up of naturally occurring amino acids and peptide bonds, or synthetic peptidomimetic structures. For example, homophenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In another embodiment, the candidate bioactive agents are naturally occurring proteins or fragments of naturally occurring proteins. Thus, for example, cellular extracts containing proteins, or random or directed digests of proteinaceous cellular extracts, may be used. In one embodiment, the libraries are of bacterial, fungal, viral, and mammalian proteins, with the latter being preferred, and human proteins being especially preferred.

In one embodiment, the candidate agents are peptides of from about 2 to about 30 amino acids, with from about 5 to about 20 amino acids being preferred, and from about 7 to about being particularly preferred. The peptides may be digests of naturally occurring proteins as is outlined above, random peptides, or random peptides. By randomized or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In another embodiment, the candidate agents are nucleic acids. By nucleic acid or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, Carbohydrate Modifications in Antisense Research, Ed. Y.S. Sanghui and P. Dan Cook; Mesmaeker et al., Bioorganic & Medicinal Chem. Lett. 4:395 (1994); Jeffs et al., J. BiomolecularNMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y.S. Sanghui and P. Dan Cook. Nucleic acids containing one or more carbocyclic sugars are also included within the definition of nucleic acids (see Jenkins et al., Chem. Soc. Rev. (1995) ppl69–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo-and ribo-nucleotides, and any combination of bases, including uracil, adenine, thymine, cytosine, guanine, inosine, xanthine, hypoxanthine, isocytosine, isoguanine, etc.

As described above generally for proteins, nucleic acid candidate agents may be naturally occurring nucleic acids, random nucleic acids, or biased random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, the candidate agent is a small molecule. The small molecule is preferably 4 kilodaltons (kd) or less. In another embodiment, the compound is less than 3 kd, 2 kd or 1 kd. In another embodiment the compound is less than 800 daltons (D), 500 D, 300 D or 200 D. Alternatively, the small molecule is about 75 D to 100 D, or alternatively, 100 D to about 200 D.

Devices for the preparation of combinatorial libraries are commercially available (see, e.g., 357 MPS, 390 NWS, Advanced Chem Tech, Louisville K.Y.; Symphony, Rainin, Woburn, Mass.; 433A Applied Biosystems, Foster City, Calif.; 9050 Plus, Millipore, Bedford, Me.).

The present invention provides methods of screening candidate bioactive agents for modulators of target protein activity. In a preferred embodiment, the methods are in vitro methods, utilizing purified or partially purified target proteins. Alternatively, the methods are in vivo methods, utilizing cells comprising target nucleic acids that can be expressed to produce target proteins, particularly when the target protein is either secreted or on the surface.

In a preferred embodiment, the methods comprise combining a target protein and a candidate bioactive agent, and evaluating the effect on the target protein's activity. By "target protein activity" or grammatical equivalents herein is meant the biological activity of the target protein. As will be appreciated by those in the art, the activity of the target protein will vary with the target protein chosen, and will be generally ascertainable by one of skill in the art of the target protein.

In a preferred embodiment, the methods of the invention comprise the addition of candidate agents to the target proteins. In general, this is done under conditions which normally allow the direct or indirect production of ADP or phosphate by the target protein. The phrase "under conditions which normally allow production or utilization of ADP or phosphate" as used herein means that all of the compositions and conditions are provided to allow the production or utilization of ADP or phosphate. Thus, the reaction which directly or indirectly produces or uses ADP or phosphate would normally occur in the absence of the modulator.

As will be appreciated by those in the art, the components are added in buffers and reagents to assay target protein activity and give optimal signals (i.e. the largest ADP or phosphate signals possible). Since the methods outlined herein allow kinetic measurements, the incubation periods are optimized to give adequate detection signals over the background.

A "modulator of a target protein which directly or indirectly produces or uses ADP or phosphate" can be any compound as described herein in the context of candidate agents which modulates the target protein's direct or indirect production or use of ADP or phosphate relative to a control.

In one aspect, the method comprises subjecting the mixture to an enzymatic reaction which uses ADP or phosphate as a substrate under conditions which normally allow the ADP or phosphate to be utilized and determining the level of activity of the enzymatic reaction. This step can be performed in conjunction with identifying a modulator of a target protein which directly or indirectly produces ADP or phosphate or independently thereof to identify a modulator of a protein which uses ADP or phosphate.

The phrase to "use ADP or phosphate" as used herein means that the ADP or phosphate are directly acted upon. In one case, the ADP, for example, can be hydrolyzed or can be phosphorylated. As another example, the phosphate can be added to another compound. As used herein, in each of these cases, ADP or phosphate is acting as a substrate.

There are a number of enzymatic reactions known in the art which use ADP as a substrate. For example, kinase reactions such as pyruvate kinases are well known. Nature, 78:632 (1956); Mol. Pharmacol, 6(1):31–40 (1970). This is a preferred method in that it allows the regeneration of ATP. In one embodiment, the level of activity of the enzymatic reaction is determined directly. For example, in a pyruvate kinase reaction, pyruvate or ATP can be measured by conventional methods known in the art.

In a preferred embodiment, the level of activity of the enzymatic reaction which uses ADP as a substrate is measured indirectly by being coupled to another reaction. For example, in one embodiment, the method further comprises a lactate dehydrogenase reaction under conditions which normally allow the oxidation of NADH, wherein said lactate dehydrogenase reaction is dependent on the pyruvate kinase reaction. Measurement of enzymatic reactions by coupling is known in the art, i.e., Nature, 178:632 (1956) and is further discussed below in regards to fluorescence.

Furthermore, there are a number of reactions which utilize phosphate. Examples of such reactions include a purine nucleoside phosphorylase reaction. This reaction can be measured directly or indirectly. The reaction can be measured directly by conventional methods known in the art.

In a preferred embodiment, the level of activity of the enzymatic reaction which uses phosphate as a substrate is measured indirectly by being coupled to another reaction. For example, in one embodiment, the method further comprises a purine analog cleavage reaction under conditions which normally allow the cleavage of the purine analog. See, PNAS, 89:4884–4887 (1992); Anal. Biochem., 246:86–95 (1997); Biochem., J., 266:611–614 (1990). Alternatively, xanthine oxidase can be used in conjunction with purine nucleoside phosphorylase to couple phosphate production to a change in the absorbance of a substrate for xanthine oxidase. Clin. Chim. Acta., 223:149–157 (1993).

In one embodiment, the detection of the ADP or phosphate proceeds non-enzymatically, for example by binding or reacting the ADP or phosphate with a detectable compound. For example, phosphomolybdate based assays may be used which involve conversion of free phosphate to a phosphomolybdate complex. J. Biol. Chem., 66:375–400 (1925). One method of quantifying the phosphomolybdate is with malchite green. Chin. Chim. Acta, 14:361–366 (1966). Alternatively, a fluorescently labeled form of a phosphate binding protein, such as the E. coli phosphate binding protein, can be used to measure phosphate by a shift in its fluorescence.

In a preferred embodiment, detection of the assay is done using a detectable label. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. The dyes may be chromophores or phosphors but are preferably fluorescent dyes, which due to their strong signals provide a good signal-to-noise ratio for detection. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, and derivatives thereof, and others described in the 6th Edition of the Molecular Probes Handbook by Richard P. Haugland, hereby expressly incorporated by reference.

The invention provides methods of screening candidate agents for the ability to serve as modulators of target protein activity. In a preferred embodiment, high throughput screening (HTS) systems are used, which can include the use of robotic systems. The assays of the present invention offer the advantage that many samples can be processed in a short period of time. For example, plates having 96 or as many wells as are commercially available can be used.

High throughput screening systems are commercially available (see, e.g., Zymark Corp., Hopkinton, Mass.; Air Technical Industries, Mentor, Ohio; Beckman Instruments, Inc., Fullerton, Calif.; Precision Systems, Inc., Natick, Mass., etc.) These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems, i.e., Zymark Corp., provide detailed protocols for the various high throughput assays.

Generally a plurality of assay mixtures are run in parallel with different agent concentrations to obtain a differential response to the various concentrations. Typically, one of these concentrations serves as a negative control, i.e., at zero concentration or below the level of detection. However, in one embodiment, any concentration can be used as the control for comparative purposes.

In one preferred embodiment, high throughput screening methods. involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics or agricultural compounds.

For example, in one embodiment, candidate agents are assayed in highly parallel fashion by using multiwell plates by placing the candidate agents either individually in wells or testing them in mixtures. Assay components, such as for example, molecular motors, protein filaments, coupling enzymes and substrates, and ATP can then be added to the wells and the absorbance or fluorescence of each well of the plate can be measured by a plate reader. A candidate agent which modulates the function of the molecular motor is identified by an increase or decrease in the rate of ATP hydroylsis compared to a control assay in the absence of that candidate agent.

A preferred HTS system is as follows. The system comprises a microplate input function which has a storage capacity matching a logical "batch" size determined by reagent consumption rates. The input device stores and, delivers on command, barcoded assay plates containing pre-dispensed samples, to a barcode reader positioned for convenient and rapid recording of the identifying barcode. The plates are stored in a sequential nested stack for maximizing storage density and capacity. The input device can be adjusted by computer control for varying plate dimensions. Following plate barcode reading, the input device can be adjusted by computer control for varying plate dimensions. Following plate barcode reading, the input device transports the plate into the pipetting device which contains the necessary reagents for the assay. Reagents are delivered to the assay plate with the pipetting device. Tip washing in between different reagents is performed to prevent carryover. A time dependent mixing procedure is performed after each reagent to effect a homogeneous solution of sample and reagents. The sequential addition of the reagents is delayed by an appropriate time to maximize reaction kinetics and readout levels. Immediately following the last reagent addition, a robotic manipulator transfers the assay plate into an optical interrogation device which records one or a series of measurements to yield a result which can be correlated to an activity associated with the assay. The timing of the robotic transfer is optimized by minimizing the delay between "last reagent" delivery and transfer to the optical interrogation device. Following the optical interrogation, the robotic manipulator removes the finished assay plates to a waste area and roceeds to transfer the next plate from pipetting device to optical interrogation device. Overlapping procedures of the input device, pipetting device and optical interrogation device are used to maximize throughput.

It is understood that the methods provided herein can be applied to a varied array of target proteins and are not limited to cytoskeletal component systems. However, for illustrative purposes, another example of the present invention is to assay for modulators of the polymerized state of cytoskeletal filament proteins actin or tubulin. In this example, the candidate agent or mixture comprising at least one candidate agent is incubated with the filament protein under conditions that would normally promote either polymerization or depolymerization. A molecular motor that is activated by the filament is then added to the assay mixture and its activity is monitored by ADP or phosphate release as discussed above. Candidate agents which increase the fraction of the filament protein in a polymerized state will be identified by an increase in the motor ATPase and those which increase the fraction of the filament protein in a depolymerized state will be identified by a decrease in the motor ATPase.

It is understood that once a modulator or binding agent is identified that it can be subjected to further assays to further confirm its activity. In particular, the identified agents can be entered into a computer system as lead compounds and compared to others which may have the same activity. The agents may also be subjected to in vitro and preferably in vivo assays to confirm their use in medicine as a therapeutic or diagnostic or in the agricultural arena.

In a preferred embodiment, approximately 1000 assays are performed per hour with very low false negative and false positive rates, with up to 10,000 assays an hour being preferred and more than 10,000 assays per hour being particularly preferred. In a particularly preferred embodiment, at least one or more of the steps regarding automated liquid handling or preferred assay design as described herein are included.

In one embodiment, the method comprises automated liquid handling.

In preferred embodiments, an antifoam or a surfactant is included in the assay mixture and wash solution. Suitable antifoams include, but are not limited to, antifoam 289 (Sigma), and others commercially available. Suitable surfactants include, but are not limited to, Tween, Tritons including Triton X-100, saponins, and polyoxyethylene ethers. This eliminates bubbles which often result in conventional methods requiring pipetting into low volume assay wells. Thus, in a preferred embodiment, the invention includes the use of an antifoam, detergent or surfactant as a reagent in a high throughput screens, including, but not limited to the screens of the invention. Generally the antifoams, detergents or surfactants are added at a range from about 0.01 ppm to about 10 ppm, with from about 1 to about 2 ppm being preferred. In a further preferred embodiment, the invention includes the use of an antifoam, surfactant or detergent when the assay requires mixing, particularly physical mixing such as shaking the microtiter plates. In an additional preferred embodiment, the invention includes the use of an antifoam, surfactant or detergent when the assay is done in microtiter plates, particularly plates with 96 wells or more, including 96, 384 and 1536 plates.

In another aspect, a round sample well is used. This helps increase the pathlength for absorbance measurements for a given assay volume and helps flatten the meniscus of the solution in each assay well. Preferably, the method comprises vigorous shaking of the sample plate following the addition of each reagent.

In a preferred embodiment herein, a preferred assay design is provided. In one aspect, the preferred assay preferably uses a multi-time-point (kinetic) assay, with at least two data points being preferred. As will be appreciated by those in the art, the interval can be adjusted to correlate with the biological activity of the protein. In the case of multiple measurements the absolute rate of the protein activity can be determined, and such measurements have higher specificity particularly in the presence of candidate agents which have similar absorbance or fluorescence properties to that of the enzymatic readout. The kinetic assay reduces the false positive rate. In an additional aspect, the kinetic rate are normalized to several control wells on each assay plate. This allows for some variation in the activity of the target proteins and the stability of assay reagents over time and thus permits screening runs of several hours.

When proteins that use ATP are included, the pyruvate kinase/lactate dehydrogenase embodiments are particularly preferred due to the advantage of ATP regeneration so that ATP concentration is constant over time.

Further regarding variation of the assays, it is understood that for a kinesin-microtubule modulator assay, the order of addition of the assay components affects the ATPase rate.

The invention further provides methods for identifying whether any two test proteins interact. Briefly, the assay is functionally similar to a yeast two-hybrid system, but relies on an increase in ATPase activity as a result of bringing two components together as a result of a protein-protein interaction. As an example, the system is described using a biological polymer binding site and a polymer stimulated ATPase, although as will be appreciated by those in the art, any two components that result in an increase in ATPase activity as a result of association can be used. For example, a first test protein (a "bait" protein), for which an interaction is sought, is joined, usually covalently, to a biological polymer binding protein, for example a cytoskeletal binding protein (such as a microtubule binding protein) to form a first target chimera. The term "chimera" or "fusion protein" as used herein refers to a protein (polypeptide) composed of two polypeptides that, while typically unjoined in their native state, typically are joined by their respective amino and carboxyl termini through a peptide linkage to form a single continuous polypeptide. It will be appreciated that the two polypeptide components can be directly joined or joined through a peptide linker/spacer.

A second test protein (a "prey" protein), is joined, again usually covalently, to an ATPase domain that is stimulated by the cytoskeletal component to form a second target chimera. Upon combination with the cytoskeletal component, the first target chimera binds to the cytoskeletal component, and if the first and second target proteins interact, the second target chimera is brought into proximity with the cytoskeletal component, and thus the ATPase activity is stimulated and can be detected. If there is no interaction, no increase in ATP production is observed.

In a preferred embodiment, the biological polymer binding protein comprises just a domain of a larger protein that comprises an ATPase domain; that is, the ATPase domain has been removed. Alternatively, the biological polymer binding protein may include the larger protein but have the ATPase domain inactivated, for example by mutation. Similarly, the ATPase domain may be either just the ATPase functional domain of a protein, or it may include a larger protein that has the binding domain inactivated.

As discussed above, the chimera proteins are generally joined covalently, for example by making fusion proteins, although covalent cross-linking can be used, or high affinity non-covalent associations can also be done, for example using binding partners such as biotin/avidin, etc. In a preferred embodiment, the fusion proteins are made using fusion genes, as is generally known in the art.

In a preferred embodiment, the target proteins should not have ATPase activity themselves, although it is possible to detect increases in activity.

Suitable biological polymers include, but are not limited to, nucleic acids including DNA and RNA, and cytoskeletal components including, but not limited to, microtubules and microfilaments (actin filaments).

Suitable biological binding sites include, but are not limited to, nucleic acid binding domains (when nucleic acids are the biological polymer), and molecular motor binding domains (in the case of cytoskeletal components).

Suitable ATPases include, but are not limited to, those that exhibit an increase (stimulation) in the presence of the biopolymer, such as DNA and RNA polymerases in the case of nucleic acids, microtubule stimulated ATPases in the case of microtubules including kinesins and dyneins, and actin stimulated ATPases such as myosins.

In a preferred embodiment, the first test protein is attached to a functional molecular motor binding domain to provide a first target chimera. The second test protein is attached to a functional microtubule stimulated ATPase domain to form a second target chimera. The first and second target chimeras are combined under conditions which normally allow activity of a motor protein which comprises a molecular motor binding domain and a microtubule stimulated ATPase domain. An increase in motor protein activity indicates interaction between the two test proteins.

Customarily one bait protein is used to test a library of test sequences as is described below; however, as will be appreciated by those in the art, the bait protein may be one of a library as well, thus forming an experimental matrix wherein two libraries (although the coding regions of the libraries could be identical) are evaluated for protein-protein interactions. In a preferred embodiment, self-activating bait proteins are filtered out from the bait protein library.

In another embodiment a method for identifying whether a candidate agent is a modulator of at least one of a first and second test protein is provided. In this case, a candidate agent is combined with the first and second chimeras as described above. A change in molecular motor activity in the presence and absence of the candidate agent indicates that the candidate agent is a modulator of at least one of the two candidate agents.

Thus, the chimeras of the present invention can be formed used recombinant techniques known in the art. The chimera can be formed at the protein level wherein two polypeptides are joined, or at the molecular level wherein a nucleic acid is formed which encodes the appropriate functional motor component and the appropriate test protein.

In a preferred embodiment, the nucleic acids encoding a chimera are used to express the respective recombinant chimera. A variety of expression vectors, including viral and non-viral expression vectors can be made which are useful for recombinant protein expression in a variety of systems, including, but not limited to, yeast, bacteria, archaebacteria, fungi, insect cells and animal cells, including mammalian cells.

The expressed chimera may also include further fusion domains including tag polypeptides. Recombinant protein is produced by culturing a host cell transformed with a nucleic acid encoding the chimera (generally as an expression vector), under the appropriate conditions that induce or cause expression of the chimera.

In a preferred embodiment, the recombinant chimera is purified following expression, as outlined above.

For using the chimeras in the assays described herein, if the two test proteins bind to one another, a complex with both chimeras comprising a functional molecular motor is formed. Thus, the binding interaction between the two test proteins can be identified by functional motor activity under conditions which would normally allow motor activity if both a functional microtubule stimulated ATPase and binding domain were present.

In the case of identifying a modulator in an assay utilizing the chimeras of the present invention, the modulator can be an activator of the motor activity. Thus, in the absence of the candidate agent, there may be no motor activity, however, in the presence of the candidate agent, motor activity occurs. Conversely, there may be significant motor activity, indicating that the two testbinding proteins interact, but this may decrease in the presence of a candidate agent. In either case, the candidate agent is identified as a modulator of at least one the two test proteins.

In a preferred embodiment, motor activity is identified by ATP hydrolysis as described above. However, it is understood that motor activity can be identified by a number of assays. Such assays include microtubule gliding, depolymerization/polymerization and any motor activity which requires both binding and ATPase activity. Therefore, in the case that the molecular motor used has another specific activity, such as involvement in mitosis or axonal transport, specific assays for those activities can be utilized.

Generally motility assays involve immobilizing one component of the system (e.g., the kinesin motor or the microtubule) and then detecting movement, or change thereof, of the other component. Thus, for example, in a preferred embodiment, the microtubule will be immobilized (e.g., attached to a solid substrate) and the movement of the kinesin motor molecule(s) will be visually detected. Typically the molecule that is to be detected is labeled (e.g, with a fluorescent label) to facilitate detection.

Methods of performing motility assays are well known to those of skill in the art (see, e.g., Hall, et al. (1996), *Biophys. J.*, 71: 3467–3476, Turner et aL, 1996, *Anal. Biochem.* 242 (1):20–5; Gittes et al., 1996, *Biophys. J.* 70(1): 418–29; Shirakawa et al., 1995, *J.Exp. Biol.* 198: 1809–15; Winkelmann et al., 1995, Biophys. J. 68: 2444–53; Winkelmann et aL, 1995, Biophys. J 68: 72S, and the like).

In addition to the assays described above for identifying ATPase activity, conventional methods can be used. For example, $P^i$ release from kinesin can be quantified. In one preferred embodiment, the ATPase activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 μL of reaction is quenched in 90 μL of cold 0.3 M PCA. Phosphate standards are used so data can be converted to mM inorganic phosphate released. When all reactions and standards have been quenched in PCA, 100 μL of malachite green reagent is added to the to relevant wells in e.g., a microtiter plate. The mixture is developed for 10–15 minutes and the plate is read at an absorbance of 650 nm. If phosphate standards were used, absorbance readings can be converted to mM Pi and plotted over time.

Additionally, in the case of methods provided herein utilizing the chimeras in accordance with the present invention, the remaining ATP can be measured using the luciferin-luciferase system. Anal. Biochem., 40:1–17 (1971).

The assays are preferably performed in a high throughput system as described herein utilizing multiwell plates and fluorescence or absorbance readouts.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

EXAMPLE

A High Throughput Assay for Modulators of the Molecular Motor Kinesin

This assay is based on detection of ADP production from kinesin's microtubule stimulated ATPase. ADP production is monitored by a coupled enzyme system consisting of pyruvate kinase and lactate dehydrogenase. Under the assay conditions described below, pyruvate kinase catalyzes the conversion of ADP and phosphoenol pyruvate to pyruvate and ATP. Lactate dehydrogenase then catalyzes the oxidation-reduction reaction of pyruvate and NADH to lactate and AND+. Thus, for each molecule of ADP produced, one molecule of NADH is consumed. The amount of NADH in the assay solution is monitored by measuring light absorbance at a wavelength of 340 nm.

Assay Components

A kinesin heavy chain construct consisting of the N-terminal 420 amino acids is used in the assay. The final 25 μl assay solution consists of the following: 5 μg/ml kinesin, 30 μg/ml microrubules, 5 μM Taxol, 0.8 mM NADH, 1.5 mM phosphoenol pyruvate, 3.5 U/ml pyruvate kinase, 5 U/ml lactate dehydrogenase, 25 mM Pipes/KOH pH 6.8, 2mM MgC12, 1 mM EGTA, 1 m MDTT, 0.1 mg/ml BSA, 0.001% antifoam 289 (Sigma), and 1 mM ATP.

Compound Plates

Potential chemical modulators of kinesin are dissolved in DMSO at a concentration of approximately 1 mg/ml, and 0.5 μl of each chemical solution is dispensed into a single well of a clear 384 well plate (Clinipate, Labsystems). On each plate, there are at least 16 wells into which pure DMSO (without a candidate compound) is dispensed. These wells serve as negative controls for comparison to the potential chemical modulators on that plate. The compound plates are made in advance and stored at 4° C., and each plate is labeled with a bar code which is used to identify the compounds on a given plate.

Instrumentation

The robotic system that runs the assay consists of a plate storage and retrieval device (Plate Stak, CCS Packard), a 96 channel automated pipetting device (Multimek, Beckman), a robotic arm (Twister, Zymark), and a plate reader for absorbance (Ultramark, BioRad). The system is controlled by a custom-built software application.

Assay Performance

A stack of compound plates is placed in the plate storage devices and plates are transferred one at a time to the automated pipetting device by the plate carrier of the Plat Stak. Each of the 384 wells are then filled with 20 µl of a solution consisting of all of the assay components described above except for ATP. The plate is then agitated at high frequency by rapidly moving the plate carrier between two positions that are separated by a few millimeters. The plate is then returned to the pipetting position. While the shaking of the plate occurs, the pipet tips are washed with a solution of 0.001% antifoam in deionized water. To start the assay, 5 µl of a second solution containing ATP is then added to each well. The solution is then mixed by a second cycle of high frequency agitation. The plate is then transferred to the plate reader by the robotic arm. In the plate reader, 10 absorbance measurements at 340 mn are taken at 12 second intervals to produce a 2 minute kinetic read for each well. While one plate is being read, the next plate is transferred to the pipetting device and prepared up to but not including the addition of the second solution. When the plate read is complete, the robotic arm transfers the plate to a waste chute and simultaneously the second solution is pipetted into the next plate so that it can be transferred to the reader to complete the cycle. The entire assay is run at room temperature ~20°C.

Data Analysis

Following data acquisition, the maximum rate of the absorbance change is calculated for each well and normalized to the average of the control wells (without compound) which were present on the same plate. The normalized rates are then entered into an Oracle database, and this allows them to be correlated with the potential chemical modulators. On each plate, the coefficient of variation of the slopes for the control wells ranges from 4–8%. Quality control is assured by monitoring for a minimal initial absorbance and a linear absorbance change.

Important Features

There are several features of this system which are important. The kinetic design which consists of multiple absorbance measurements dramatically improves the specificity of the assay over a single endpoint measurement. First, the rate of the reaction is to a first approximation independent of small differences between wells in the time from the start of the reaction to the first reading, and as a result, the overall variation in the data is reduced. Second, the rate of the absorbance change is not affected by having a chemical compound which absorbs light of the same wavelength.

The presence of control wells in each plate and the subsequent normalization of the data to those wells allows data to be taken for several hours despite some degradation of the enzyme activities which results from the aging of the solutions. This also improves the reproducibility of the data.

The presence of antifoam in the solution and the tip washing solution improves overall liquid handling by reducing the number of trapped bubbles in the small wells and helps flatten the fluid meniscus in each well for more reliable absorbance measurements. Additional features which improve liquid handling are the vigorous shaking of the plate described above, and the round shape of the wells in the microplates used.

The assay components and the performance of the assay are optimized together to match the overall read time with the rate of kinesin's ADP production. In this example, the rate of absorbance change is approximately 150–250 mOD/min. This corresponds to the production of approximately 2 µM ADP/sec. In addition to optimizing the rate of ADP production, the read time must be long enough for the rate of NADH consumption to reach steady state beyond an initial lag time of several seconds. In some cases, the order of addition of the reagents can have a significant affect on the rate of ADP production. In the above example, the optimal rate is achieved by premixing all reagents except for the compound of interest and ATP.

What is claimed is:

1. A high throughput assay method for rapidly identifying a compound that modulates function of a target protein wherein said target protein produces ADP or phosphate and said method comprises:

a) adding a compound to a mixture comprising a target protein which produces ADP or phosphate under conditions which normally allow the production of ADP or phosphate;

b) subjecting the mixture to an enzymatic reaction, wherein said enzymatic reaction uses ADP or phosphate as a substrate under conditions which normally allow the ADP or phosphate to be utilized; and c) determining NADH consumption as a measure of ADP production; wherein a change in measure of NADH consumption between the presence and absence of said compound indicates that said compound is a modulator of said target protein, wherein up to about 10,000 assays can be performed per hour; the assays are performed in microtiter plates having 96 wells or more; and the assay mixture further comprises a surfactant or antifoam.

2. The method of claim 1 wherein said determining occurs by a fluorescent, lumininescent, radioactive or absorbance readout.

3. The method of claim 1 wherein said enzymatic reaction is determined at multiple time points.

4. The method of claim 1 wherein a plurality of compounds are added.

5. The method of claim 1 wherein a plurality of compounds are added to a plurality of target proteins.

6. The method of claim 1 wherein said compounds are added using a robotic system.

7. A method of identifying a compound as a modulator of an ATPase, said method comprises:

a) adding a compound to a mixture comprising the ATPase under conditions which normally allow for the production of ADP;

b) contacting the reaction mixture from step (a) with a kinase and a phosphorylated substrate to form ATP from ADP and a dephosphorylated substrate;

c) contacting the dephosphorylated substrate from step (b) with NADH and a dehydrogenase under oxidative-reductive conditions whereby NADH is consumed; and d) measuring NADH consumption as a measure of ADP production;
  wherein a change in measure of NADH consumption between the presence and absence of said compound indicates that said compound is a modulator of said ATPase.

8. The method of claim 7 wherein a plurality of compounds are added.

9. The method of claim 8 wherein said compounds are added using a robotic system.

10. The method of claim 7 wherein a plurality of compounds are added to a plurality of ATPases.

11. The method of claim 7 wherein said kinase is pyruvate kinase, said phosphorylated substrate is phosphoenol pyruvate, and said dephosphorylated substrate is pyruvate.

12. A high throughput method for rapidly identifying a compound that modulates function of a target protein wherein said target protein produces ADP or phosphate and said method comprises:
  a) adding a compound to a mixture comprising a target protein which produces ADP or phosphate under conditions which normally allow the production of ADP or phosphate, wherein said mixture further comprises a surfactant or antifoam;
  b) reacting the ADP or phosphate produced in step (a) with a detectable compound; and
  c) measuring ADP production indirectly by measuring said detectable compound,
    wherein a change in level of ADP production between the presence and absence of said compound indicates that said compound is a modulator of said target protein function, and
    wherein up to about 10,000 assays can be performed per hour and wherein the assays are performed in microtiter plates having 96 wells or more.

13. The method of claim 12, wherein said detectable compound comprises a molecule having at least one detectable element, isotope, or chemical label attached thereto.

14. The method of claim 13, wherein said element, isotope or chemical label is detected by a fluorescent, luminescent, radioactive, or absorbance readout.

15. The method of claim 12, wherein a plurality of compounds are added.

16. The method of claim 12, wherein a plurality of compounds are added to a plurality of target proteins.

17. The method of claim 16, wherein said candidate agents are added using a robotic system.

18. The method of claim 1, wherein the target protein is an ATPase, kinase, GTPase, phosphatase, or phosphorylase.

19. The method of claim 18, wherein the target protein is a kinesin.

20. The method of claim 19, wherein the target protein is Kin2, chromokinesin, KiflA, KSP, CENP-E, MCAK, HSET, or Kif15.

21. The method of claim 18, wherein the target protein is myosin.

22. The method of claim 18, wherein the target protein is dynein.

23. A method of identifying a compound as a modulator of a target protein wherein said target protein regulates an enzyme that produces ADP or phosphate, and said method comprises:
  a) adding a compound to a mixture comprising said target protein and said enzyme under conditions which normally allow the production of ADP or phosphate;
  b) utilizing the ADP or phosphate as a substrate in an enzymatic reaction; and
  c) measuring NADH consumption as a measure of ADP production;
    wherein a change in measure of NADH consumption between the presence and absence of said compound indicates that said compound is a modulator of said target protein.

24. The method of claim 23, wherein said target protein is an activator of an ATPase.

25. The method of claim 24, wherein said target protein is an actin filament or a microtubule.

26. The method of claim 23, wherein said target protein is a filament binding protein.

27. The method of claim 23, wherein said target protein is a regulatory protein.

28. The method of claim 27, wherein said target protein regulates the binding of myosin to actin.

29. The method of claim 28, wherein said target protein is troponin or tropomyosin.

30. The method of claim 7, wherein said ATPase is a kinesin.

31. The method of claim 30, wherein said ATPase is Kin2, chromokinesin, Kif1A, KSP, CENP-E, MCAK, HSET, or Kif15.

32. The method of claim 7, wherein said ATPase is myosin.

33. The method of claim 7, wherein said ATPase is dynein.

34. The method of claim 23 wherein said measuring occurs by a fluorescent, luminescent, radioactive or absorbance readout.

35. The method of claim 23 wherein said measuring is repeated at multiple time points.

36. The method of claim 23 wherein a plurality of compounds are added.

37. The method of claim 23 wherein a plurality of compounds are added to a plurality of target proteins.

38. The method of claim 36 wherein said compounds are added using a robotic system.

* * * * *